United States Patent [19]

Tobari et al.

[11] 4,211,532
[45] Jul. 8, 1980

[54] TEST COMPOSITION, METHOD AND A TEST STICK FOR DETECTION OF CHLORIDE ION IN COW'S MILK

[75] Inventors: Shizen Tobari, Tachikawashi; Mariko Nakano, Hokkaido, both of Japan

[73] Assignee: Toyo Roshi Kaisha Ltd., Tokyo, Japan

[21] Appl. No.: 924,376

[22] Filed: Jul. 13, 1978

[30] Foreign Application Priority Data

Oct. 27, 1977 [JP] Japan .................................. 52-128167

[51] Int. Cl.² ............................................ G01N 33/04
[52] U.S. Cl. ...................................... 23/231; 252/408; 422/56
[58] Field of Search ............... 23/231, 230 R; 422/56; 252/408

[56] References Cited

U.S. PATENT DOCUMENTS

| | | | |
|---|---|---|---|
| 2,676,874 | 4/1954 | Devine | 422/56 X |
| 3,092,463 | 6/1963 | Adams, Jr. et al. | 422/56 |
| 3,329,486 | 7/1967 | Rupe | 422/56 |
| 3,434,801 | 3/1969 | Scherr | 422/56 |
| 3,552,929 | 1/1971 | Fields et al. | 422/56 |

*Primary Examiner*—Arnold Turk
*Attorney, Agent, or Firm*—Wenderoth, Lind & Ponack

[57] ABSTRACT

Test composition and test stick for detection of chloride ion in cow's milk, which composition comprises a protected silver chromate colloidal substance, a surface active agent and a buffer agent having a pH value ranging from 2 to 7, and which test stick comprises a carrier, protected silver chromate colloidal substance, a surface active agent and a buffer agent having a pH value ranging from 2 to 7; and a method for producing the test stick.

10 Claims, 1 Drawing Figure

Test stick prepared according to Example 2

Test stick prepared according to Example 2

TEST COMPOSITION, METHOD AND A TEST STICK FOR DETECTION OF CHLORIDE ION IN COW'S MILK

BACKGROUND OF THE INVENTION

Field of the Invention

The present invention relates to a test composition for detection of chloride ion in cow's milk, and a test stick for the same purpose as well as a method for manufacturing such a test stick.

In recent years, mastitis, an infection of the udder, causing production of abnormal milk, has been increasing, partially due to introduction of milking machines and this automation.

At present, about 550,000 cows among some 1,800,000 cows in Japan are treated by veterinarians for mastitis, and 10,000–20,000 cows die from mastitis.

As for the diagnosis due to the mastitis, veterinarians detect such symptoms as hardening of the udder, fever and loss of appetite, and various inspection methods have been put into practice, one of which is measurement of chloride ion in cow's milk.

The significance of measurement of chloride ion in milk is that when permeability of the mammary glands is accelerated by the mastitis, chloride ions together with bicarbonates, sulfates, sodium, ionic calcium serum albumine from the blood abnormally increases in the milk, and this acceleration of permeation which is one sign of the mastitis is detected to make the diagnosis.

As a method for detecting chloride ion in milk, the Hayden method, Sino-test No. 7 method, modified Hayden method, and Schales-Schales method have been conventionally known and have been in practice. The Hayden method is a qualitative method which determines the positivity (+) or the negativity (−), while the Schales-Schales method can analyze chloride ion in the milk with high accuracy but is disadvantageous in that the preparation of reagents and quantitative analysis are complicated, thus requiring great skill and longer time for analysis. Further this method requires special analysis apparatus and thus is considered not to be suitable for use as an outdoor clinical testing method. Therefore, development of a simplified method for measurement of chloride ion in the milk which can be performed by an inexperienced person easily in the field has been strongly sought to faciliate an earlier diagnosis.

SUMMARY OF THE INVENTION

The present invention have made extensive studies to develop such a simplified method which can overcome the disadvantages of the prior art, and have completed the present invention.

One of the objects of the present invention is to provide a test composition suitable for detecting chloride ion in cow's milk. Another object of the present invention is to provide a test stick for detecting chloride ion in cow's milk.

Still another object of the pesent invention is to provide a method for producing the test stick.

The composition according to the present invention comprises a protected silver chromate colloidal substance, a surface active agent and a buffering agent having a pH ranging from 2 to 7.

The present invention has advantages such that chloride ion in cow's milk can be detected easily and quickly at any place, and it is possible to perform a quantative analysis by comparing a standard color chart with the accurately developed color.

DETAILED DESCRIPTION OF THE PRESENT INVENTION

The present invention will be described in more details with reference to the attached drawing.

Figure 1:
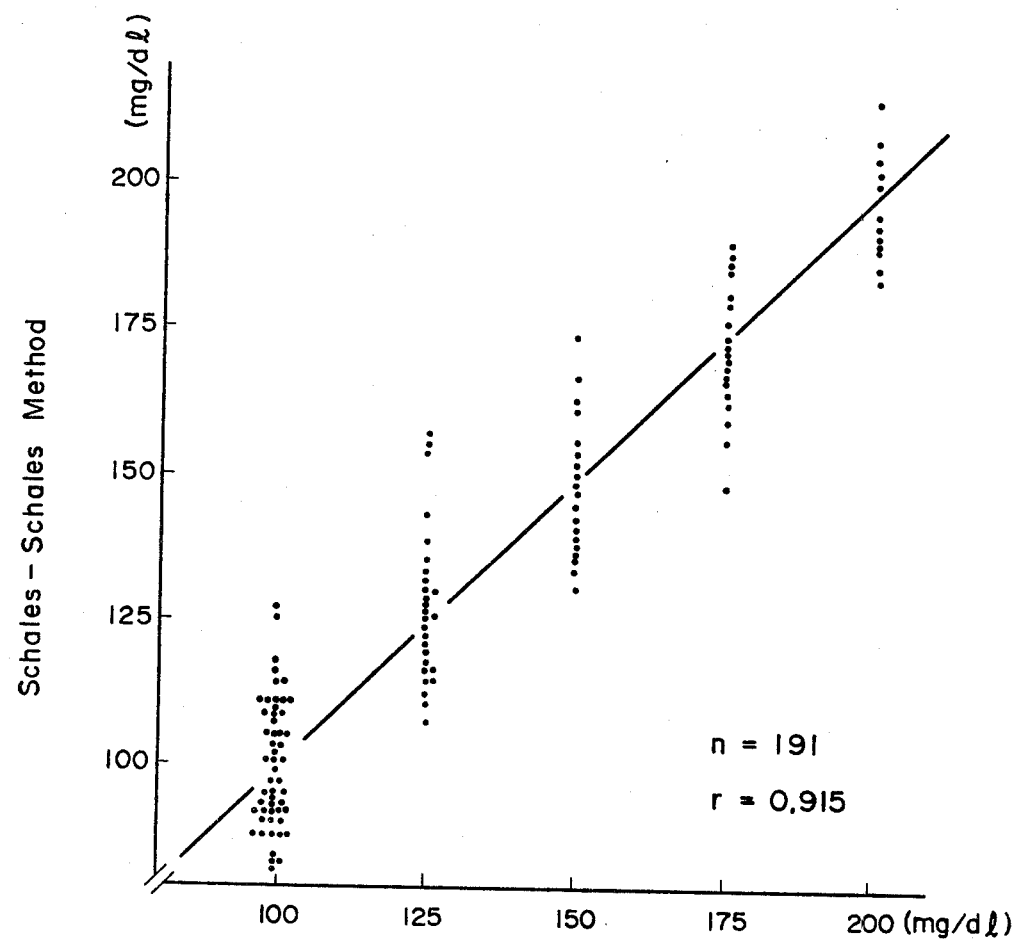
FIG. 1 shows correlation between the measurements obtained by the Schales-Schales method and the measurements obtained by the test stick (Example 2) according to the present invention.

The present invention is based on the following principle.

Silver chromate is converted by chloride ion into white silver chloride, and in this reaction the dark brown color of the silver chromate is changed to yellow in proportion to the amount of chloride ion. Thus,

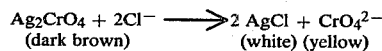

$$Ag_2CrO_4 + 2Cl^- \longrightarrow 2\,AgCl + CrO_4^{2-}$$
(dark brown)      (white) (yellow)

The above reaction is a kind of precipitation reaction, caused by the difference in solubility product between silver chromate and silver chloride, and when the chloride ion is present the equilibrium moves in the direction to produce silver chloride which has a smaller solubility product. The solubility products are:

$$S_{AgCl} = [Ag^+][Cl^-] = 1.78 \times 10^{-10}\ (25°\ C.)$$

$$S_{Ag_2CrO_4} = [Ag^+]^2[CrO_4^{2-}] = 9 \times 10^{-12}\ (25°\ C.)$$

Hereinbelow the protected silver chromate colloidal substance according to the present invention will be described. As stated hereinbefore the present invention is based on the fact that a silver chromate is converted by chloride ion into a white silver chloride and that the dark brown color of silver chromate is changed to yellow in proportion to the amount of chloride ion taking part in the reaction. In this connection, it has been found that the silver chromate itself, when dispersed in water, produces a very unstable hydrophobic colloid. This hydrophobic colloid immediately coagulates and settles down, and it is very difficult to maintain it in a uniformly dispersed state for a long period of time. Therefore, in the present invention, the hydrophobic colloidal particles of silver chromate are covered with a substance which forms a hydrophilic colloid so as to give the hydrophobic colloidal particles the nature of the hydrophilic colloid in order to stabilize the hydrophobic colloid of silver chromate. Therefore, in the present invention, the hydrophobic colloidal particles of silver chromate which are converted into hydrophilic colloidal particles by the covering thereon of a hydrophilic-colloid-forming substance are called "a protected silver chromate colloidal substance", and the substance which forms a hydrophilic colloid is called "a protective colloidal substance".

The protected silver chromate colloidal substance is prepared as below. A chromate, such as sodium chromate, potassium chromate, ammonium chromate, magnesium chromate, magnesium-potassium chromate and lithium chromate, and a protective colloidal substance, such as gum arabic, albumin, gelatine, polyvinyl alcohol and polyvinyl pyrrolidone, are mixed and dissolved in water, and an aqueous solution of a silver salt, such as silver nitrate, silver acetate and silver sulfate, is added thereto to obtain a protected silver chromate colloidal substance.

In the present invention, the pH value of the solution of protected silver chromate colloidal substance is very important, and with pH values larger than 7.0, a silver hydroxide is formed, and with a further oxidation a silver oxide is formed, while with pH values less than 2 the silver chromate may sometime be dissolved. Therefore, the pH value must be adjusted between 2.0 and 7.0 with a buffer agent. In this meaning, the pH-buffer agent is essential to the present invention.

In the present invention, any type of buffer agent such as acetic acid type, citric acid type, malic acid type, succinic acid type, borate type and glycol type, may be used so far as it falls within the pH range from 2.0 to 7.0.

According to the present invention, a surface active agent is added so as to promote compatibility and permeation of the milk (containing fat, protein etc.) into the reagent, thereby eliminating irregular color development. Without a surface active agent, irregular color development is necessarily caused because the milk contains various substances so that it is very difficult to judge the color and thus no practical utility is assured.

In the present invention, any surface active agent may be used so far as it does not react with the milk components, such as white blood corpuscles. However, a non-ionic surface active agent, such as sorbitan fatty acid ester, polyoxyethylene alkyl ether, polyoxyethylenealkyl-phenol ether is advantageous.

The test composition according to the present invention may be used in the form of solution or tablet, but it is very advantageous to impregnate an absorbing strip-like carrier such as filter paper with the solution and use it as a testing stick for detection of chloride ion in the milk in the field. In the actual application, when the test stick is dipped in the milk for a period of about 15 seconds, the test stick takes various colors depending on the concentration of chloride ion, and the colors thus developed are compared with a standard color chart prepared on the basis of actual measurements. In this way, the amount of chloride ion in the milk can be quantitatively determined with great ease.

A description will now be made on the preparation of the test stick according to the present invention.

First, 0.5–2 parts by weight of chromate and 1 to 2 parts by weight of the protective colloidal substance are mixed and dissolved in 100 to 150 parts by weight of distilled water. Then 1–2 parts by weight of silver nitrate is dissolved in 100 to 150 parts by weight of distilled water and the solution is gradually dropped into the above chromate solution by means of a buret to obtain a solution of the protected silver chromate colloidal substance. For satisfactory stirring of the solution a stirrer is used. The solution thus obtained is called Solution I.

Next, 3–7 parts by weight of a buffer agent having a pH value ranging from 2.0 to 7.0, and 0.5 to 2 parts by weight of a surfactant are dissolved in 100 to 150 parts by weight of distilled water. The solution thus obtained is called Solution II.

An absorbing carrier, such as a filter paper or disc is fully impregnated with the Solution I for 5 to 30 seconds, and taken out of the solution, shaking off excessive solution, and placed on a clean, flat plate. In this case, full care should be taken so as to avoid any vacancy between the absorbing carrier and the plate, which would cause irregular color development. After confirming that there is no vacancy, the carrier is placed horizontally and dried in a hot air dryer.

The drying is an operation for the purpose of impregnating the carrier surface with silver chromate as much as possible, and the drying heat is given directly to the carrier surface and thus the drying proceeds from the surface. The solution of protected silver chromate colloidal substance impregnated in the back side adhering to the plate and in the inner portion of the carrier is condensed chromatographically in the surface portion.

The principle of the present invention is the precipitation reaction between silver chromate and chloride ion, and this reaction is remarkably retarded in the inner portion and back side of the carrier, but it progresses in the surface portion. Therefore, the test stick, on the surface of which the protected silver chromate colloidal substance is condensed, is very useful for detecting chloride ion in the milk.

If the carrier is not dried on the plate, the concentration of the protected silver chromate colloidal substance is uniform through the surface, inner portion and back surface of the carrier, so that even after the reaction in the surface portion is completed, non-reacted substances are retained in the inner portion and back surface of the carrier, which lead to misjudgement of the color development. Also the remaining silver chromate impairs the adhesion of both-side adhesion tape to the carrier and causes unsatisfactory adhesion in the preparation of test the stick.

As the flat plate on which the carrier is placed for drying, a glass plate, a metal plate, and a plastic plate are desirable.

After the drying of the carrier on the flat plate, the carrier, e.g. a filter paper, is peeled off the plate and immersed in Solution II, and taken out of the solution, shaking off the excessive solution. Then the carrier is hung and dried in a hot air oven.

The absorbing carrier, such as a filter paper and a disc, has a great influence on the performance of the test stick. For example, in case of a cellulose filter paper, it is desirable that it is 0.2–0.5 mm in thickness and 100–200 g/m$^2$ in weight, and has a water absorption height of 7.0–10.0 cm/10 min. and contains not more than 0.1% of ash.

Regarding the drying conditions, it is most advantageous to dry the carrier with a hot air of low humidity at a temperature ranging from 50° to 80° C. for 30 to 60 minutes.

DESCRIPTION OF PREFERRED EMBODIMENTS

The present invention will be more clearly understood from the following embodiments.

EXAMPLE 1

2.0 g of potassium chromate and 2.0 g of gum arabic are dissolved in 100 g of distilled water under stirring. Meanwhile, 2.0 g of silver nitrate is dissolved in 100 g of distilled water under stirring and this solution is gradually dropped into the potassium chromate-gum arabic solution by means of a buret. Further 6.0 g of sodium citrate, 4.0 g of citric acid, and 2 ml of surface active agent (polyoxyethylene sorbitan mono laurate) are added to the solution, and the solution is stirred by means of a stirrer. The solution thus prepared shows no separation (precipitation) of silver chromate and is very stable and it maintains a uniform condition for a long period of time, and is very useful for detection of chloride ion in cow's milk.

For practical use of the solution, 1 ml of milk is taken in a small test tube, and 1 ml of the solution is gradually dropped down thereto with good stirring. After 15 seconds the milk develops various colors depending on the concentration of chloride in the milk, and these colors are compared with a standard color chart or tube (prepared on the basis of several groups of milk having different chloride ion contents ranging from a practically possible low concentration to a practically possible high concentration) to quantitatively determine the chloride ion content in the cow's milk.

EXAMPLE 2

Preparation of Solution I 1.0 g of potassium chromate and 1.5 g of gum arabic are dissolved in 100 g of distilled water under stirring. Meanwhile, 1.0 g of silver nitrate is added to 100 g of distilled water under stirring and this solution is slowly added by drops to the potassium chromate-gum arabic solution by means of a buret to prepare a solution of protected silver chromate colloidal substance. For this preparation, the solution is stirred by means of a stirrer during the addition of the silver chromate solution and for 30 minutes after the addition. The solution thus obtained is called Solution I.

Preparation of Solution II 6.0 g of sodium citrate, 4.0 g of citric acid, and 1 ml of a surface active agent (polyoxyethylene sorbitan mono laurate) are dissolved in 100 g of distilled water under stirring. The final solution thus obtained is called Solution II.

Then filter paper No. 514 (manufactured by Toyo Roshi K.K., Japan) is impregnated with Solution I for 5 seconds and taken out from the solution, shaking off the exessive solution, and tightly placed on a glass plate, and dried at 50° C. for 40 minutes in a hot air drier while being maintained in a horizontal state therein.

The dried filter paper is peeled off the glass plate and is impregnated with Solution II, and after shaking off excessive solution from the paper, the paper is hung in an air oven to dry the paper at 80° C. for 20 minutes.

On the whole of the back side of the dried filter paper thus obtained, a both-side adhesion tape (Nitto 501 M) is stuck, and the paper is cut into sticks of 5×10 mm, and these cut sticks are adhered to the tip end of a synthetic resin film of 5×85 mm to prepare a test stick for detection of chloride ion in cow's milk.

EXAMPLE 3

Preparation of Solution I 1.0 g of sodium chromate and 1.5 g of gelatin are dissolved in 100 g of distilled water under stirring. Meanwhile, 1.0 g of silver sulfate is dissolved in 100 g of distilled water under stirring, and this solution is dropped into the sodium chromate-gelatin solution by means of a buret to prepare a solution of protected silver chromate colloidal substance. For this preparation, the solution is stirred by means of a stirrer during the addition of the silver chromate solution and for 30 minutes after the addition. The final solution thus obtained is called Solution I.

Preparation of Solution II 5.0 g of sodium acetate, 2.0 g of acetic acid and 1 ml of a surface active agent (polyoxyethylene sorbitan mono palmitate) are dissolved in 100 g of distilled water under stirring. The solution thus obtained is called Solution II. In a similar way as in Example 2, a test stick for detection of chloride ion in cow's milk is prepared.

EXAMPLE 4

Preparation of Solution I 2.0 g of ammonium chromate, and 2.0 g of polyvinylalcohol are dissolved in 100 g of distilled water under stirring. Meanwhile, 2.0 g of silver acetate is dissolved in 100 g of distilled water and this solution is gradually dropped into the ammonium chromate-polyvinylalcohol solution by means of a buret to prepare a solution of protected silver chromate colloidal substance. For the preparation of the final solution the solution is well stirred during the addition of the silver chromate solution and for 30 minutes after the addition. The final solution thus obtained is called Solution I.

Preparation of Solution II 4.0 g of sodium malate, 3.0 g of malic acid and 1 ml of a surface active agent (polyoxyethylene sorbitan mono oleate) are dissolved in 100 g of distilled water under stirring. The solution thus obtained is called Solution II.

In a similar way as in Example 2, a test stick for detection of chloride ion in cow's milk is prepared.

In order to illustrate the utility of the composition according to the present invention, the test stick prepared according to Example 2 was used for quantative determination of chloride ion in milk for 191 cases and at the same time the quantitative determination was performed by Schales-Schales method. The results are compared in FIG. 1. There is a high degree of correlation between them, as high as 0.915 of correlation function.

The colors developed by the above test sticks were used for the quantative determination of chloride ion according to the six color graduations (corresponding to 0, 100, 125, 150, 175, 200 mg/dl) of the standard color chart, and when the color developed by the test stick is intermediate between the above graduations, it is possible to read an intermediate value. In this way, a more accurate quantitative determination is assured.

For investigating reproductivity of the measurement of chloride ion in milk by the test stick according to the present invention, the amount of chloride ion in milk was determined accurately by the Schales-Schales process; five samples of milk having different chloride ion concentrations were measured ten times respectively.

The results shown in Table 1 indicate that in any of the five samples almost the same measurements were obtained.

Table 1

| | Reproductivity of Measurements by the Test Stick according to the Present Invention | | | | | | | | | |
|---|---|---|---|---|---|---|---|---|---|---|
| mg/dl | 1 | 2 | 3 | 4 | 5 | 6 | 7 | 8 | 9 | 10 |
| 106.2 | 100 | 100 | 100 | 100 | 125 | 100 | 100 | 100 | 100 | 100 |
| 126.7 | 125 | 125 | 125 | 125 | 125 | 125 | 125 | 150 | 125 | 125 |

Table 1-continued

| | Reproductivity of Measurements by the Test Stick according to the Present Invention | | | | | | | | | |
|---|---|---|---|---|---|---|---|---|---|---|
| mg/dl | 1 | 2 | 3 | 4 | 5 | 6 | 7 | 8 | 9 | 10 |
| 150.9 | 150 | 150 | 175 | 125 | 150 | 125 | 150 | 150 | 150 | 150 |
| 173.3 | 175 | 175 | 175 | 175 | 175 | 175 | 175 | 175 | 175 | 175 |
| 201.3 | 200 | 175 | 200 | 200 | 200 | 200 | 200 | 200 | 200 | 200 |

Thus, the composition and the test stick for detection of chloride ion in cow's milk according to the present invention have a high degree of reproductivity and accuracy, and are capable of measuring chloride ion in cow's milk with a very simple operation as compared with conventional simplified methods such as the Hayden method and Schales-Schales method, so that it is possible for not only veterinarians but even dairy farmers to make diagnosis of mastitis in cows.

What is claimed is:

1. A composition for detecting chloride ion in cow milk, comprising a protected silver chromate colloidal substance, a surface active agent and a buffer agent having a pH value from 2 to 7.

2. A composition according to claim 1, wherein the protected silver chromate colloidal substance is colloidal particles of silver chromate covered by a hydrophilic colloid-forming substance.

3. A composition according to claim 2, wherein the hydrophilic colloid-forming substance is gum arabic, albumin, gelatin, polyvinyl alcohol or polyvinyl pyrrolidone.

4. A method of detecting chloride ion in cow milk, comprising mixing the composition of claim 1 with a test sample of the cow milk, and comparing the color developed in the resultant mixture with a standard color chart which shows color graduations corresponding to differing concentrations of chloride ion.

5. A composition for detecting chloride ion in cow milk, comprising an absorbent carrier carrying a protected silver chromate colloidal substance, a surface active agent and a buffer agent having a pH value from 2 to 7.

6. A composition according to claim 5, wherein the protected silver chromate colloidal substance is colloidal particles of silver chromate covered by a hydrophilic colloid-forming substance.

7. A composition according to claim 6, wherein the hydrophilic colloid-forming substance is gum arabic, albumin, gelatin, polyvinyl alcohol or polyvinyl pyrrolidone.

8. A method of detecting chloride ion in cow milk, comprising immersing the composition of claim 5, in the form of a test stick, into the cow milk, and comparing the color developed on the resultant test stick with a standard color chart which shows color graduations corresponding to differing concentrations of chloride ion.

9. A method for producing a test stick for detection of chloride ion in cow milk, comprising impregnating an absorbent carrier with a solution of a protected silver chromate colloidal substance, drying the impregnated carrier on a plate, immersing the dried carrier in a solution containing a surface active agent and a buffer agent having a pH value from 2 to 7, and drying the resultant carrier.

10. A method according to claim 9, wherein the solution of the protected silver chromate colloidal substance is obtained by the dropwise addition of a solution of 1-2 parts by weight of silver nitrate in 100-150 parts by weight of distilled water to a solution of 0.5-2 parts by weight of a chromate and 1-2 parts by weight of a protective colloidal substance in 100-150 parts by weight of distilled water, said addition being carried out while stirring said solution of chromate and protective colloidal substance.

* * * * *